United States Patent
Ishibashi

(10) Patent No.: US 7,378,102 B2
(45) Date of Patent: May 27, 2008

(54) DICLOFENAC SODIUM ORAL PHARMACEUTICAL

(75) Inventor: Nobuyuki Ishibashi, Ono (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 42 days.

(21) Appl. No.: 10/508,327

(22) PCT Filed: Mar. 27, 2003

(86) PCT No.: PCT/JP03/03803

§ 371 (c)(1),
(2), (4) Date: Oct. 12, 2004

(87) PCT Pub. No.: WO03/080040

PCT Pub. Date: Oct. 2, 2003

(65) Prior Publication Data

US 2005/0214360 A1  Sep. 29, 2005

(30) Foreign Application Priority Data

Mar. 27, 2002  (JP) .............................. 2002-089321

(51) Int. Cl.
*A61K 31/19* (2006.01)
*A61K 31/195* (2006.01)
*A61K 9/00* (2006.01)
*A61K 9/48* (2006.01)

(52) U.S. Cl. ...................... 424/400; 424/451; 514/566; 514/567

(58) Field of Classification Search ................ 424/451, 424/400, 401; 514/568, 567
See application file for complete search history.

(56) References Cited

U.S. PATENT DOCUMENTS

| 4,944,949 A | 7/1990 | Story et al. |
| 5,785,976 A * | 7/1998 | Westesen et al. ........... 424/400 |
| 5,789,244 A * | 8/1998 | Heidrun et al. .......... 435/320.1 |

FOREIGN PATENT DOCUMENTS

| JP | A 63-277617 | 11/1988 |
| JP | A 7-508013 | 9/1995 |
| JP | A 8-507515 | 8/1996 |
| JP | A 10-152431 | 6/1998 |
| JP | A 2002-509103 | 3/2002 |
| WO | WO 94/20072 A1 | 9/1994 |
| WO | WO 00/72827 A2 | 12/2000 |

OTHER PUBLICATIONS

Gennaro, Remington's Pharmaceutical Sciences, 1990, 18th Ed., p. 1658.*
Fini et al., European Journal of Pharmaceutical Sciences, 1996;4(4):231-238.*
Remington's Pharmaceutical Sciences, 18th ed., 1990, pp. 207-208.*

* cited by examiner

*Primary Examiner*—San-ming Hui
(74) *Attorney, Agent, or Firm*—Oliff & Berridge, PLC

(57) ABSTRACT

The present invention relates to a diclofenac sodium oral pharmaceutical containing diclofenac sodium, a nonionic surfactant, a cholic acid derivative as an absorption promoting agent, and a glycerin or a glycol.

The oral pharmaceutical has a rapid-acting effect and a good internal absorption even under non-fasting condition. Further, the pharmaceutical can be processed in a hard capsule pharmaceutical by filling it in a hard capsule as such, and has an excellent internal absorption under non-fasting condition, similarly to suppositories.

8 Claims, 2 Drawing Sheets

DICLOFENAC SODIUM ORAL PHARMACEUTICAL

TECHNICAL FIELD

The present invention relates to a rapid-acting diclofenac sodium oral pharmaceutical.

BACKGROUND ART

Diclofenac sodium (Monosodium 2-(2,6-dichloroanilino) phenyl acetate, $C_{14}H_{10}C_{12}NNaO_2$) is a nonsteroidal drug having analgesic, anti-inflammatory and anti-rheumatic effects which was developed by CIBA-GEIGY AG in Switzerland (now, Novartis Pharma AG) in 1965. This drug has a strong action and a low toxicity compared with indomethacin or the like, and therefore is widely subjected to current clinical use.

The commercially available diclofenac sodium pharmaceuticals include tablets, delayed-release pharmaceuticals and suppositories, etc. Among them, oral pharmaceuticals are formulated for rapid-acting effect. However, it is recommended to avoid taking them on an empty stomach as they have side effects such as stomach discomfort.

However, the absorption of diclofenac sodium oral pharmaceuticals is outstandingly effected on whether or not a meal has been eaten. When they are taken after eating, the initial absorption of diclofenac sodium is outstandingly reduced in the amount and delayed in the rate compared with the case where they are taken on an empty stomach, and in some cases, the maximum absorption is confirmed at several hours to ten and several hours after taking them, and also individual difference is large in the absorption thereof.

Therefore, in case where an rapid-acting effect and certainty are taken seriously, it is the present state that the pharmaceuticals are used in most cases in a form of suppository. However, there are many patients who are reluctant to use the suppositories, and therefore the suppositories can not be used as conveniently as oral pharmaceuticals. Consequently, today there is a strong request for diclofenac sodium oral pharmaceuticals having a rapid-acting effect and certainty similarly to the suppository even in case where it is taken on a non-empty stomach.

It has been already known that in order to increase an internal absorption of a pharmaceutical agent that is slightly soluble in water, the pharmaceutical agent is formulated with a surfactant to increase the solubility of the pharmaceutical agent to water.

As the prior document, Japanese Patent Laid-open No. Sho 63-277617 discloses a medicine composition for oral administration from which micelles are formed, comprising an nonsteroidal anti-inflammatory agent such as diclofenac, and a nonionic surfactant such as polyoxyethylated surfactant, sorbitan fatty acids or the like. In addition, the examples of this document describe a pharmaceutical comprising diclofenac acid and polyoxyethylated castor oil. However, this document does not describe at all the above-mentioned problem on the absorption of diclofenac sodium pharmaceutical under non-fasting condition nor means for solving the problem. Further, this document does not describe as surfactant cholic acid derivatives that are varieties of anionic surfactants.

In addition, Japanese Patent Laid-open No. Hei 8-507515 discloses a particle-suspension of colloidal solid particles in which a pharmaceutical agent being slightly soluble in water is captured with solid particles that are emulsified and stabilized by adding a lipid that is insoluble or slightly soluble in water at room temperature to nonionic surfactant and bile salts containing propylene glycol as dispersant, and this document discloses that the pharmaceutical agent includes diclofenac. However, this document has no concrete disclosure on diclofenac pharmaceuticals. Also, this document does not describe problems to be solved by the present invention nor means for solving the problems similarly to the above-mentioned Japanese Patent Laid-open No. Sho 63-277617.

As mentioned above, although it was known that diclofenac being slightly soluble in water is mixed with surfactants in order to increase solubility and dispersibility, it was not necessary to use surfactants for diclofenac sodium having a higher water-solubility, and therefore the mixing of surfactants has not been considered.

DISCLOSURE OF THE INVENTION

Under the above-mentioned circumstances, the present inventor earnestly investigated and repeatedly considered to make diclofenac sodium oral pharmaceuticals rapid-acting under non-fasting condition by producing pharmaceuticals comprising a variety of substances such as surfactants, absorption promoting agent, melting point modifiers, solubilizing agents and viscosity modifiers, etc. and by using them in a test of kinetics in rat blood under non-fasting condition and in a dissolution test. As the results, the inventor found that diclofenac sodium oral pharmaceuticals have an excellent absorption under non-fasting condition by mixing a nonionic surfactant, a cholic acid derivative represented by deoxycholic acid as absorption promoting agent, and a glycerin or a glycol as melting point modifier (used for lowering melting point) with diclofenac sodium. Consequently, the present invention was completed on the basis of the finding.

That is, the present invention provides a diclofenac sodium oral pharmaceutical characterized by containing diclofenac sodium, a nonionic surfactant, a cholic acid derivative as an absorption promoting agent, and a glycerin or a glycol.

In addition, the present invention provides a diclofenac sodium oral pharmaceutical, which is filled in a hard capsule.

The rapid-acting diclofenac sodium oral pharmaceutical of the present invention is in a liquid state in which mixed compositions are dissolved each other or in a solid state in which the mixed compositions in a liquid state are solidified, and is not in a state of a particle-suspension in which a pharmaceutical agent is captured with carrier solid particles that is disclosed in Japanese Patent Laid-open No. Hei 8-507515.

And, the pharmaceutical of the present invention can be processed in an oral pharmaceutical by filling it in a hard capsule as such. The material of this hard capsule is preferably hydroxypropylmethylcellulose (HPMC). The rapid-acting diclofenac sodium oral pharmaceutical of the present invention can be also filled in a soft capsule, processed in an oral liquid by dissolving it in water or the like, pulverized by mixing it with a pulverization agent, granulated or processed in tablets. Further, these pharmaceuticals can be combined with a delayed-release pharmaceutical.

BEST MODE FOR CARRYING OUT THE INVENTION

Figure 1:
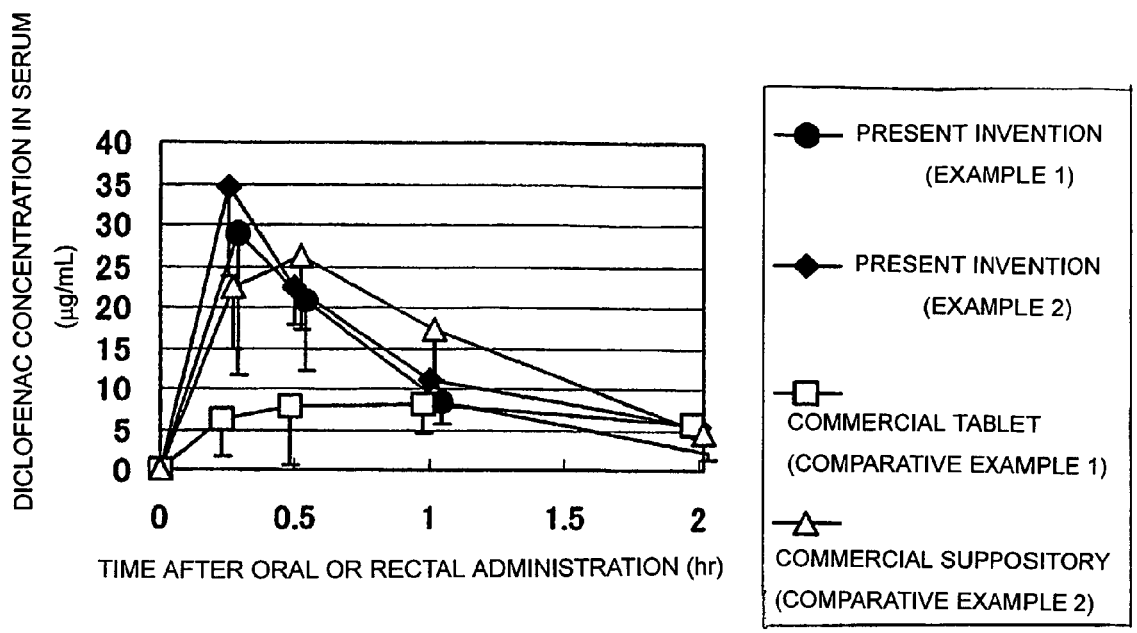
FIG. 1 is a graph showing initial kinetics in blood of rat (n=6, non-fasting condition) to which the pharmaceuticals produced in Example 1 and 2 according to the present invention, and a tablet (Comparative Example 1) and a suppository (Comparative Example 2) of commercially available diclofenac sodium was administered.

Hereinafter, each component of the oral pharmaceutical to be mixed along with the active ingredient in the present invention, diclofenac sodium will be described in further detail.

The nonionic surfactant used for the diclofenac sodium oral pharmaceutical of the present invention is a surfactant having little toxicity in oral administration, and can be used in a combination of two or more. Examples of the nonionic surfactant include saturated polyglycolated glycerides, polyoxyethylene sorbitan fatty acid esters (polysorbates) and polyglycerin fatty acid esters, polyoxyethylene glycerin fatty acid ester deoxycholic acids, sucrose fatty acid esters, lecithin derivatives, propyleneglycol fatty acid esters, glycerin fatty acid esters, sorbitan fatty acid esters, polyoxyethylene sorbit fatty acid esters, polyoxyethylene lanolin/lanolin alcohol/bees wax derivatives, polyoxyethylene castor oil/hardened castor oil, polyoxyethylene sterol/hydrogenated sterol polyethyleneglycol fatty acid esters, polyoxyethylene alkyl ethers, polyoxyethylene polyoxypropylene alkyl ethers, polyoxyethylene phenyl ethers, polyoxyethylene alkyl phenyl formaldehyde condensation products, and polyoxyethylene polyoxypropylene glycol, and the like. Among them, nonionic surfactants having a relatively high HLB value (HLB=10 to 20) are preferable.

The cholic acids derivatives as the absorption promoting agent used for the diclofenac sodium oral pharmaceutical of the present invention includes for example lithocholic acid, deoxycholic acid, glycodeoxycholic acid, taurodeoxycholic acid, chenodeoxycholic acid, glycochenodeoxycholic acid, taurochenodeoxycholic acid, ursodeoxycholic acid, glycoursodeoxycholic acid, tauroursodeoxycholic acid, cholic acid, glycocholic acid, taurocholic acid, ursocholic acid, glycoursocholic acid, tauroursocholic acid and the salts thereof such as sodium salt or potassium salt, etc. These cholic acid derivatives may be used in a combination of two or more.

The melting point modifiers used for the diclofenac sodium oral pharmaceutical of the present invention includes for example glycerin, polyethyleneglycols, propyleneglycols or a combination of two or more selected from these compounds. These melting point modifiers are used also as solubilizing agents.

The formulating ratio of the pharmaceuticals is as follows. The nonionic surfactant can be added in an amount of 0.05 to 20 parts by weight, preferably 1 to 5 parts by weight based on 1 part by weight of diclofenac sodium. In addition, the absorption promoting agent and melting point modifier may be added in an appropriate amount according to need, preferably based on 1 part by weight of diclofenac sodium, the absorption promoting agent is added in an amount of 0.01 to 5 parts by weight, preferably 0.05 to 0.5 part by weight, and the melting point modifier is added in an amount of 0.1 to 10 parts by weight, preferably 1.0 to 5.0 parts by weight.

A preferable formulation example for the pharmaceutical of the present invention comprises diclofenac sodium, and saturated polyglycolated glyceride (for example Gelucire 44/14 (trade name) manufactured by Gattefosse in France) or polyoxyethylene sorbitan fatty acid ester (for example, NIKKOL TS-10 (trade name), Polysorbate 60, manufactured by Nikko Chemicals Co., Ltd.) as nonionic surfactant, deoxycholic acid as absorption promoting agent and propylene glycol as melting point modifier. More preferable formulation example for the pharmaceutical comprises diclofenac sodium, and deoxycholic acid, hexaglyceryl monolaurate (for example NIKKOL Hexaglyn 1-L (trade name), manufactured by Nikko Chemicals Co., Ltd.) and propylene glycol, preferably in a weight ratio of 1:0.1:3.5:1.8.

The diclofenac sodium oral pharmaceuticals were prepared by using the surfactants, absorption promoting agents and melting point modifiers as mentioned above. The pharmaceuticals showed the most excellent initial kinetics in rat blood (non-fasting) and a high dissolution rate in the first fluid of Disintegration Test specified in The Japanese Pharmacopoeia.

Further, the diclofenac sodium oral pharmaceuticals of the present invention may contain other solubilizing agents, viscosity modifiers and excipients which are commonly used for pharmaceuticals, if necessary.

EXAMPLES

Next, the present invention will be concretely described by showing examples to which the present invention is not be limited.

Example 1

In a glass bottle with screw-cap, 100 g of pulverized diclofenac sodium was weighed, then 350 g of saturated polyglycolated glyceride (Gelucire 44/14 (trade name) manufactured by Gattefosse in France), 10 g of deoxycholic acid and 120 g of propyleneglycol were added therein. A magnet bar was placed in the glass bottle which then was sealed with a screw cap. The resulting mixture sealed in the glass bottle was stirred in a water bath at 70° C. After diclofenac sodium and deoxycholic acid were dissolved, the resulting formulations were filled in a hard capsule (about 2 mm x about 8 mm) in an amount containing 5 mg of diclofenac sodium in hot state with an injector to obtain a rapid-acting diclofenac sodium pharmaceutical. The resulting hard capsule pharmaceutical was allowed to stand at room temperature for at least one day in order to be stabilized.

Example 2

350 of polyoxyethylene sorbitan fatty acid ester (NIKKOL TS-10 (trade name), Polysorbate 60, manufactured by Nikko Chemicals Co., Ltd.) was used in the place of saturated polyglycolated glyceride used in Example 1, and a pharmaceutical was obtained according to the procedures of Example 1.

Example 3

|  | (parts by weight) |
|---|---|
| Pulverized diclofenac sodium | 1 |
| Deoxycholic acid | 0.1 |
| NIKKOL Hexaglyn 1-L | 3.5 |
| (hexaglyceryl monolaurate, HLB = 14.5, manufactured by Nikko Chemicals Co., Ltd.) | |
| Propylene glycol | 1.8 |

According to the above-mentioned formulation, an appropriate amount of Hexaglyn 1-L was weighed in a glass bottle with screw-cap, and then other remaining components mentioned above were added therein. A magnet bar was placed in the glass bottle which then was sealed with a screw cap. The resulting mixture sealed in the glass bottle was stirred in a water bath while heating at nearly 70° C. After solid contents were completely dissolved, the resulting formulations were filled in a hard capsule in an amount containing 5 mg of diclofenac sodium in hot state with an injector.

The resulting capsule pharmaceutical was allowed to stand at room temperature for at least one day in order to be stabilized. Even after standing, diclofenac sodium and deoxycholic acid were not recrystallized, and the obtained pharmaceutical remained stable.

Comparative Example 1

Commercially available diclofenac sodium pharmaceutical (trade mark: Voltaren Tablet, one tablet (about 150 mg) contains 25 mg of diclofenac sodium, manufactured by Novartis Pharma AG) was scraped down with a cutter in such a manner that the scraped pharmaceutical (about 30 mg) contains diclofenac sodium in the same amount (5 mg) as that in the above-mentioned test pharmaceutical. The resulting scraped pharmaceutical was used as oral pharmaceutical.

Comparative Example 2

Commercially available diclofenac sodium pharmaceutical (trade mark: Voltaren Suppo, one suppository (about 1 g) contains 25 mg of diclofenac sodium, manufactured by Novartis Pharma AG) was scraped down with a cutter in such a manner that the scraped pharmaceutical (about 0.2 g) contains diclofenac sodium in the same amount (5 mg) as that in the above-mentioned test pharmaceutical, and that the pharmaceutical has a sharpen tip in order to be easily inserted in the anus. The resulting scraped pharmaceutical was used as suppository.

Test Example 1

Test of Kinetics in Rat Blood on Concentration

Each of the above-mentioned pharmaceuticals was orally or rectally administered to rats under non-fasting condition.

After rats (wister strain, male, body weight on arrival: 230 g) were preliminarily fed for one week, a rat was placed in a cage, and for 24 hours from the day before the test to the day thereof the rats were placed under fasting condition where only water was fed, and thereafter about 0.5 g of a solid feed was fed. 30 minutes later, six rats which ate completely the feed were used per each test condition. After slightly anesthetizing the rats with ether, the pharmaceuticals of Examples 1 to 3 and Comparative Example 1 were orally administered by using a catheter reaching the stomach. The suppository of Comparative Example 2 was rectally administered by inserting it from the anus. Then 4 ml of water was orally administered and then every ca. 15 minutes, ca. 30 minutes and ca. 120 minutes, blood was collected from each rat, diclofenac in the serum was measured (measurement method: HPLC method), and the concentration in the serum was calculated from the measured value.

FIG. 1 is a graph showing initial kinetics in blood, the data in which were plotted with concentration of diclofenac in serum of rat (non-fasting) after administration of the pharmaceutical of Example 1 or 2, or Comparative Example 1 or 2 as ordinate and time as abscissa.

As shown in this graph, it is understood that the pharmaceuticals produced in Examples 1 and 2 according to the present invention are excellent in initial kinetics in blood compared with commercially available diclofenac sodium tablet (Comparative Example 1) and that the pharmaceuticals of the present invention have kinetics in blood near to that of commercially diclofenac sodium suppository (Comparative Example 2) rather than that of commercially available diclofenac sodium tablet.

Figure 2:
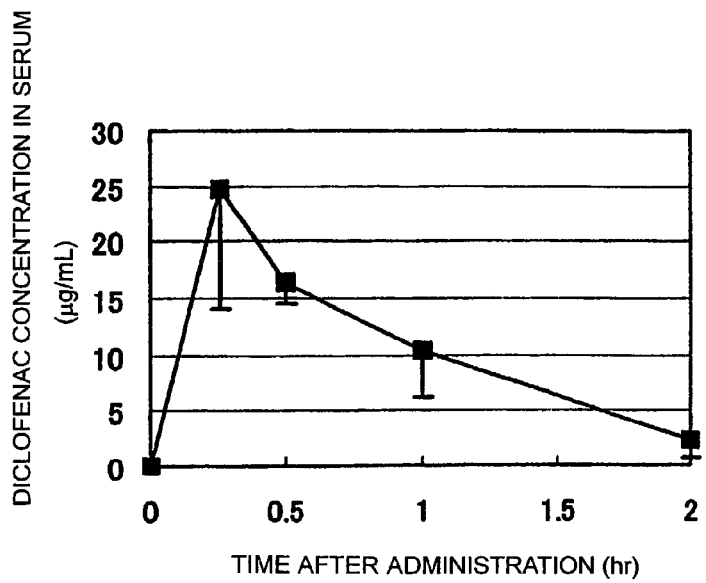
FIG. 2 is a graph showing initial kinetics in blood of rat (n=6, non-fasting condition) to which the pharmaceuticals produced in Example 3 according to the present invention.

In addition, FIG. 2 is a graph showing initial kinetics in blood, the data in which were plotted with concentration of diclofenac in serum of rat (non-fasting) after administration of the pharmaceutical of Example 3 as ordinate and time as abscissa.

It is understood that the pharmaceutical produced in Example 3 indicates also an excellent initial kinetics in blood similarly to those produced in Examples 1 and 2 according to the present invention.

Test Example 2

Dissolution Test

Figure 3:
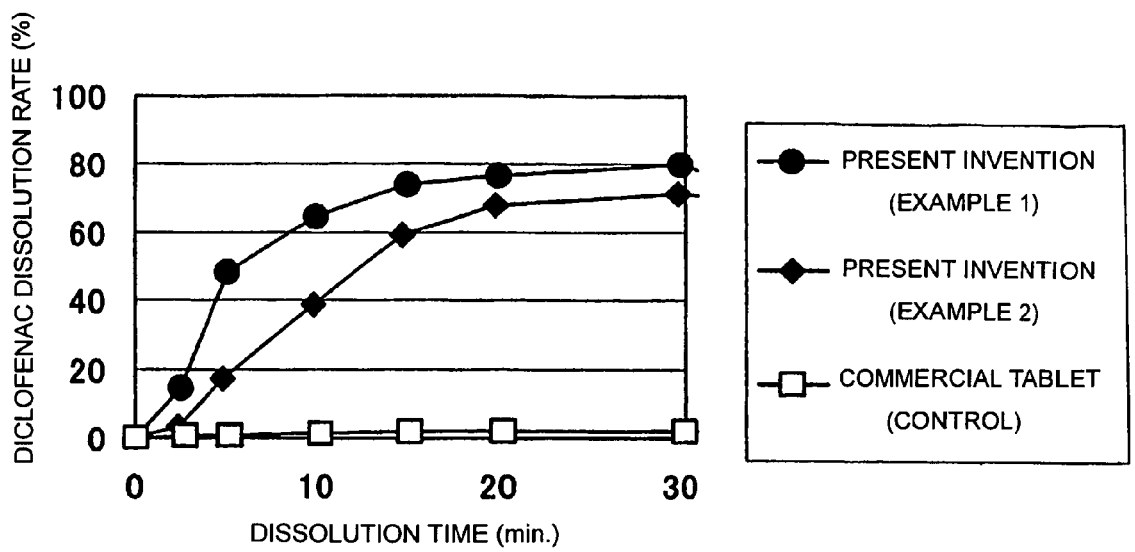
FIG. 3 is a graph showing the results of the dissolution test on the pharmaceuticals indicated in Examples 1 and 2 according to the present invention and a commercially available diclofenac sodium tablet.

Rapid-acting diclofenac sodium pharmaceuticals were prepared by filling in a hard capsule, pharmaceutical formulations prepared in Example 1 or 2 containing diclofenac sodium in an amount of 25 mg. These pharmaceuticals filled in a hard capsule and commercially available diclofenac sodium tablet (containing diclofenac sodium in an amount of 25 mg) were subjected to a dissolution test by the method (paddle method, 50 rotations/minute, dissolution fluid (the first fluid of according to Disintegration Test specified in The Japanese Pharmacopoeia (artificial gastric juice), pH 1.2, 900 mL, 37° C.)) according to Disintegration Test specified in The Japanese Pharmacopoeia. About 2.5, 5, 10, 15, 20 and 30 minutes after starting the test, the dissolution fluid was taken out, the concentration of diclofenac sodium dissolved from the pharmaceutical was measured and the dissolution rate was calculated therefrom The results are shown in the graph of FIG. 3. It is understood that the pharmaceuticals produced in Examples 1 and 2 according to the present invention have a higher dissolution rate than commercially available diclofenac sodium tablet.

Figure 4:
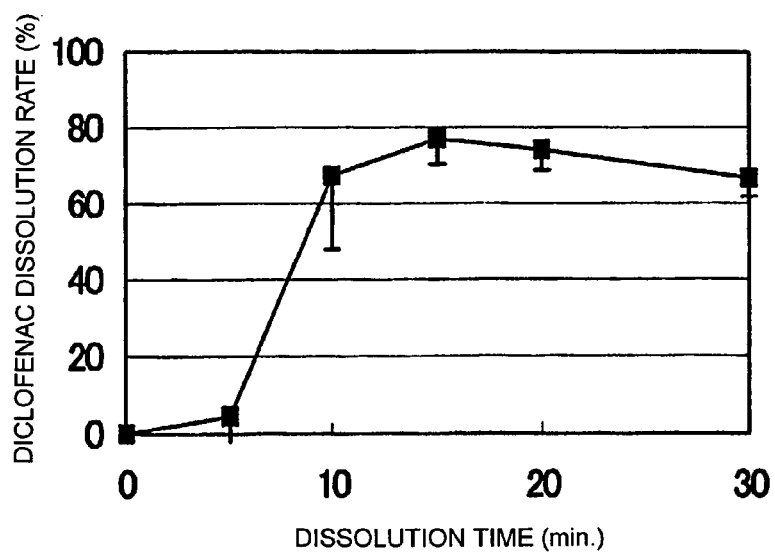
FIG. 4 is a graph showing the results of the dissolution test (n=6) on the pharmaceutical indicated in Example 3 according to the present invention and a commercially available diclofenac sodium tablet.

In addition, the pharmaceutical formulations prepared in Example 3 were filled in a hard capsule so as to contain diclofenac sodium in an amount of 25 mg and allowed to stand at room temperature for one day or more in order to be stabilized. This pharmaceutical filled in a hard capsule was subjected to a dissolution test by the method (paddle method, 100 rotations/minute, dissolution fluid (the first fluid of according to Disintegration Test specified in The Japanese Pharmacopoeia (artificial gastric juice), pH 1.2, 900 mL, 37° C.)) according to Disintegration Test specified in The Japanese Pharmacopoeia. The results are shown in the graph of FIG. 4. It is understood from this graph that the pharmaceutical produced in Example 3 has dissolution characteristics similar to the pharmaceuticals produced in Examples 1 and 2.

It is clear from these results of the examples in which diclofenac sodium shows an excellent initial kinetics in blood of rat in a non-fasting state and a high dissolution rate in the dissolution tests that the diclofenac sodium oral pharmaceuticals of the present invention have unique physical properties compared with commercially available oral pharmaceuticals and are excellent in internal absorption even in non-fasting state.

INDUSTRIAL APPLICABILITY

As described above, the diclofenac sodium oral pharmaceutical of the present invention which is formulated according to the present invention and used under non-fasting condition has a rapid-acting effect comparable to the suppository thereof. Therefore, the pharmaceutical can be effectively used for cure as oral pharmaceutical which patients can accept easily on administration thereof.

The invention claimed is:

1. An oral pharmaceutical comprising a diclofenac sodium, a nonionic surfactant, a cholic acid derivative as an absorption promoting agent, and a glycerin or a glycol, wherein the cholic acid derivative is selected from the group consisting of lithocholic acid, deoxycholic acid, glycodeoxycholic acid, taurodeoxycholic acid, chenodeoxycholic acid, glycochenodeoxycholic acid, taurochenodeoxycholic acid, ursodeoxycholic acid, glycoursodeoxycholic acid, tauroursodeoxycholic acid, cholic acid, glycocholic acid, taurocholic acid, ursocholic acid, glycoursocholic acid, tauroursocholic acid and the salts thereof, wherein the pharmaceutical is in a liquid state in which the diclofenac sodium, the nonionic surfactant, the cholic acid derivative, and the glycerin or the glycol are dissolved.

2. The oral pharmaceutical according to claim 1, wherein the pharmaceutical contains 0.05 to 20 parts by weight of the nonionic surfactant based on 1 part by weight of the diclofenac sodium, 0.01 to 5 parts by weight of the cholic acid derivative as the absorption promoting agent based on 1 part by weight of the diclofenac sodium, and 0.1 to 10 parts by weight of the glycerin or glycol based on 1 part by weight of the diclofenac sodium.

3. The oral pharmaceutical according to claim 1, which is filled in a hard capsule.

4. The oral pharmaceutical according to claim 2, which is filled in a hard capsule.

5. The oral pharmaceutical according to claim 1, further comprising a delayed-release pharmaceutical.

6. The oral pharmaceutical according to claim 2, further comprising a delayed-release pharmaceutical.

7. The oral pharmaceutical according to claim 3, further comprising a delayed-release pharmaceutical.

8. The oral pharmaceutical according to claim 4, further comprising a delayed-release pharmaceutical.

* * * * *